(12) United States Patent
Auberger

(10) Patent No.: US 10,111,426 B2
(45) Date of Patent: Oct. 30, 2018

(54) BIOCIDAL MATERIALS

(75) Inventor: Stephan Auberger, Neuvillers sur Fave (FR)

(73) Assignee: SALVECO, Saint Die des Vosges (FR)

( * ) Notice: Subject to any disclaimer, the term of this patent is extended or adjusted under 35 U.S.C. 154(b) by 226 days.

(21) Appl. No.: 13/982,903

(22) PCT Filed: Feb. 21, 2012

(86) PCT No.: PCT/FR2012/050367
§ 371 (c)(1),
(2), (4) Date: Jul. 31, 2013

(87) PCT Pub. No.: WO2012/114039
PCT Pub. Date: Aug. 30, 2012

(65) Prior Publication Data
US 2013/0309336 A1 Nov. 21, 2013

(30) Foreign Application Priority Data
Feb. 25, 2011 (FR) ...................... 11 51546

(51) Int. Cl.
*A61K 36/00* (2006.01)
*A01N 37/36* (2006.01)
*A01N 65/00* (2009.01)
*A01N 65/22* (2009.01)
*A01N 65/28* (2009.01)

(52) U.S. Cl.
CPC ............ *A01N 37/36* (2013.01); *A01N 65/00* (2013.01); *A01N 65/22* (2013.01); *A01N 65/28* (2013.01)

(58) Field of Classification Search
None
See application file for complete search history.

(56) References Cited

U.S. PATENT DOCUMENTS

| 8,541,356 | B2* | 9/2013 | Saint Victor | 510/438 |
| 8,574,628 | B2* | 11/2013 | Scholl et al. | 424/484 |
| 2002/0055446 | A1* | 5/2002 | Perron et al. | 510/119 |
| 2005/0032668 | A1* | 2/2005 | Pedersen et al. | 510/499 |
| 2010/0101605 | A1* | 4/2010 | Saint Victor | 134/6 |

FOREIGN PATENT DOCUMENTS

| EP | 1146112 A1 | 10/2001 |
| EP | 1167510 A1 | 1/2002 |
| WO | 2007018907 A1 | 2/2007 |

OTHER PUBLICATIONS

International Search Report for corresponding International Application No. PCT/FR2012/050367.
English translation of International Preliminary Report on Patentability.

* cited by examiner

*Primary Examiner* — Christopher R Tate
*Assistant Examiner* — Russell G Fiebig
(74) *Attorney, Agent, or Firm* — Andrew W. Chu; Craft Chu PLLC

(57) ABSTRACT

A novel generation of biocidal materials is provided that do not pose any specific risks to the environment or health. The active substances and additives that make up the biocidal materials according to the invention originate from plants, agricultural products, and renewable resources, and are furthermore completely biodegradable. The various uses of said novel biocidal materials are also described.

7 Claims, 1 Drawing Sheet

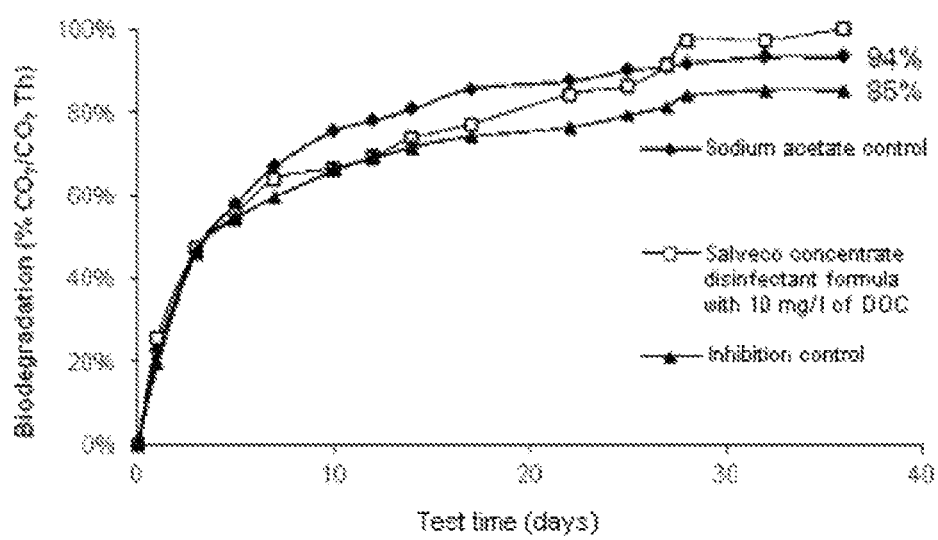

BIOCIDAL MATERIALS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a novel generation of biocidal products of plant origin which do not pose any chrome risks to health or the environment and which have very little acute impact on health or the environment. Indeed, the active substances and the adjuvants that make up the biocidal products according to the invention are of plant and renewable origin, and are, moreover, completely, naturally and rapidly biodegradable. The various uses of these novel biocidal products are also claimed.

2. Description of Related Art Including Information Disclosed Under 37 CFR 1.97 and 37 CFR 1.98

Biocidal products are commonly used in a wide variety of products including household and industrial disinfectants, insecticides, wood treatment products, repellents, etc. Biocidal products are intended to destroy, repel or render ineffective organisms judged to be harmful, for instance bacteria, viruses and fungi, to prevent the action thereof or to combat them in any other way via a chemical or biological action. There are therefore products which are chemically or biologically active and, consequently capable of having harmful effects on humans, animals and/or the environment.

A biocide is generally characterized by its field of application: bactericide, fungicide, virucide, insecticide, controlling vertebrates. Bactericides have an action against bacteria. Fungicides have an action against certain fungi and certain yeasts. Antivirals have an action against certain viruses. Insecticides have an action against insects. The latter category has an action against certain vertebrates (for example: rodent pests).

Biocidal active agents can therefore pose a major risk to human health (from an etymological point of view, "bios" means "life" and "-cide" means "which kills"), and animal health, but also to the environment through spreading or discharge. Indeed, biocidal activators can act for a long time, can spread, can be partially degraded or not at all degraded depending on their nature; they are then considered to be (bio)accumulatable. There is therefore a real advantage to developing biocidal products which are effective against harmful organisms but which are capable of being completely degraded naturally and of reducing the direct risks (linked to "acute" toxicity) or indirect risks (linked to chronic toxicity) to humans and animals.

International awareness regarding this subject has resulted in the adopting of European regulations and directives (REACH: 1907/2006 and Biocides: 98/8/EC), the objective of which is to limit the marketing, of dangerous chemical substances and to strictly regulate the use thereof.

The biocidal product market for Europe represents a volume of 300 000 to 750 000 metric tons per year (study of the impact of the Biocides directive 98/8/EC—2007). There is therefore a considerable advantage to using biocidal products which do not pose or pose significantly fewer dangers to humans, animals and/or the environment, while at the same time being effective at low concentration, and which are of plant and renewable origin and completely biodegradable.

Biocidal products can be used to clean and disinfect all types of surfaces. The active substances of which they are composed are generally active ingredients of chemical origin, sometimes active ingredients of natural origin, or else a mixture of the two.

In order to develop biocidal products which are not toxic and/or harmful to humans and the environment, and which are also biodegradable and biocompatible for humans, biocides of natural origin have been developed.

Indeed, biocidal products of plant origin appear to be the most suitable for meeting these combined objectives. The majority of biocidal solutions contain a washing base combined with a disinfectant base. However, these products do not necessarily have the same biocidal effectiveness or the same ease of use as biocidal solutions containing chemico-synthetic active agents.

U.S. patent application Ser. No. 12/624,113 describes multifunctional wipes referred to as "green", since the support is considered biodegradable, which are impregnated with a biocidal solution. The solution described contains a washing composition combined with a disinfectant/hygiene composition. The washing composition contains nonionic surfactants such as surfactants derived from sugars, from polyols, from alkyl ethers and from alkyl carbonates. It also contains cosurfactants of ionic: anionic, cationic, zwitterionic or amphoteric, nature. The disinfectant composition contains at least one active agent selected from essential oils, colloidal silver, organic acids, or mixtures of these components. It can also contain metals and metal salts. The composition cart be completed with binders, pH modifiers and other adjuvants depending on the use envisioned. The biocidal wipes which are the subject of that document have the disadvantage of not being completely biodegradable and of not being completely consisting of elements of renewable natural origin. It is a ready-to-use, and therefore diluted, impregnating "juice" which is not based on synergy making it possible to have an active concentrate.

There is therefore a need to develop a long-lasting and safe alternative to the use of chemico-synthetic products, which makes it possible to obtain a biocidal effectiveness and an ease of use of product to be diluted and ready-to-use product which are at least equivalent to the chemico-synthetic products on the professional market. It is therefore advisable to have a superconcentrated product which can be dilatable in water before use.

BRIEF SUMMARY OF THE INVENTION

The present invention relates to a novel generation of biocidal formulations for cleaning and disinfecting all surfaces. Their environmental impact is very limited, or even zero, and in any event it is not considered to be worrying. This is because these biocidal formulations are derived from renewable agricultural plant resources and the entire formulation is also completely biodegradable. The active substance of the biocidal formulations according to the invention is at least one organic acid of plant origin. This organic acid may be derived directly from an agricultural resource, or from a transformed agricultural resource.

BRIEF DESCRIPTION OF THE SEVERAL VIEWS OF THE DRAWINGS

FIG. 1 represents the curves of results of degradation with respect to $CO_2Th$.

DETAILED DESCRIPTION OF THE INVENTION

The present invention describes a concentrated biocidal formulation of plant origin, characterized in that it contains:
  between 0.01% and 20% of chelating agent;
  between 0.03% and 25% of nonionic surfactants of polyol type, and preferably between 0.03% and 25% of nonionic surfactants of glycoside, polyglycerol ester or sorbitan ester type;
  between 0.03% and 25% of anionic surfactants, preferably of carboxylate or polycarboxylate type;
  between 0.1% and 75% of one or more organic acids;
  between 0.001% and 8% of natural fragrance;
and in that it is completely biodegradable and completely derived from renewable agricultural plant resources. In addition, the ingredients used in the composition do not pose any specific risks to the environment or health.

The percentages expressed in the context of the present invention represent the percentages by weight of the compounds relative to the total weight of the biocidal formulation.

The nonionic surfactants of glycoside or polyglycerol type, for the purpose of the invention, are nonionic surfactants of the type polyols with glycoside units, i.e. alkyl polyglycosides, or polyglycerol units.

Preferably, the surfactants of polyglycerol type used in the concentrated biocidal formulation are at least one of the compounds selected from monoesters or diesters of fatty acid condensed with glycerol or polyglycerols. Mention may be made, for example, of polyglyceryl-2 laurate, polyglyceryl-5 laurate, polyglyceryl-4 caprate, polyglyceryl-3 palmitate and monoglyceryl laurate.

Preferably, the surfactants of sorbitan ester type used are selected from the following esters, which may or may not be ethoxylated: sorbitan sesquioctanoate and sorbitan laurate.

In addition to a very low environmental impact compared with the prior art, the biocidal formulations according to the invention exhibit a synergistic effect between the organic acid(s) and the nonionic surfactant and/or the anionic surfactant and/or the chelating agent.

Among the organic acids usable in the composition of the biocidal formulations according to the present invention, mention will in particular be made of acetic acid, formic acid, citric acid, sorbic acid, lactic acid, succinic acid, tartaric acid, malic acid and pyruvic acid. The choice of the organic acid is made according to the field of application of the biocidal formulations and to the target organisms to be eliminated or the growth of which it is desired to slow down or block. In one particular embodiment, the organic acid(s) is (are) lactic acid and citric acid. In one preferred embodiment, only lactic acid is used. Indeed, (L+) lactic acid is one of the essential elements of human metabolism, but also of the metabolism of animals and of microorganisms. It is the (L+) form which appears to be the natural form of lactic acid. Lactic acid intrinsically exhibits interference properties on microorganisms since it acts directly on intracellular pH and also on their energy cycle. There is therefore an antimicrobial action by inhibition of their growth (for *Escherichia coli*, inter alia). What is even more advantageous and has recently been demonstrated is the fact that lactic acid has a considerable stabilizing effect combined with a buffering effect when it is combined with certain surfactants and/or other antimicrobial agents such as ethanol or hydrogen peroxide ($H_2O_2$). It has also been observed that certain surfactants such as sodium lauryl sulfate (SLS) and sodium alkyl sulfonate (SAS) could greatly facilitate the penetration of (L+) lactic acid into target microorganisms. Moreover, in the presence of ethanol, the amount of (L+) lactic acid required in order to eliminate *Escherichia coli* colonies is reduced (U.S. Pat. No. 4,647,458). This is also confirmed by combining (L+) lactic acid and hydrogen peroxide (EP 0 423 922). This organic acid which, furthermore, is completely biodegradable and can be obtained from renewable natural resources therefore appears to be entirely suitable for integrating the composition of biocidal products. The organic acid(s) is (are) present in the formulation according to the invention in a proportion of from 0.1% to 75%.

Consequently, in one particular embodiment according to the present invention, the concentrated biocidal formulation of plant origin contains:
  between 0.01% and 20% of chelating agent;
  between 0.03% and 25% of nonionic surfactants such as polyols, preferably with glycoside or polyglycerol units, or sorbitan esters;
  between 0.03% and 25% of anionic surfactants, preferably of carboxylate or polycarboxylate type;
  between 0.1% and 75% of lactic acid;
  between 0.001% and 8% of natural fragrance;
and is completely biodegradable and completely derived from renewable agricultural plant resources.

The nonionic surfactants which are part of the composition of the biocidal product according to the invention are preferentially selected from alkyl polyols of polyglycoside type, polyglycerol esters and sorbitan esters. These compounds are derived from renewable agricultural resources such as coconut oil alcohol or polyglucose from corn. The carbon-based chains used for the syntheses of these surfactants may be branched or unbranched, but preferably linear, with a chain length of between 4 and 20 and preferably 6 and 18 carbon atoms, depending on the intended uses for the biocidal product. Moreover, these compounds do not cause any skin irritation in humans.

The anionic surfactants which are part of the composition of the biocidal product according to the invention are preferentially selected from carboxylic acid salts of alkyl polyethoxylates/propoxylates and/or polyols of the polyglycoside and/or polyglycerol type. The salts are derived from alkali metals (K, Na, etc.) or alkaline-earth metals (Ca, Mg, etc.) and are combined with acid chemical structures so as to form surfactants of the alkyl carboxylate and/or alkyl sulfate type. They are derived from renewable agricultural resources and are biodegradable. The carbon-based chains used for the synthesis of these surfactants may be branched or unbranched, with a chain length of between 6 and 20 carbon atoms, according to the uses intended for the biocidal product. Among the anionic surfactants commonly used, the biocidal formulations preferentially contain ethoxylated or nonethoxylated fatty acid salts.

Alternatively or in addition, the anionic surfactants used are preferably chosen from at least one sodium or ammonium salt of alkyl sulfates, of alkyl glucose carboxylates, of alkyl ether carboxylate, of alkyl phosphate, of alkyl ether phosphate, of alkyl sulfosuccinamate, of alkyl sulfosuccinate and of alkyl sulfoacetate. The conjugated acid forms of such anionic surfactants can also be used. Advantageously, the anionic surfactants which are part of the formulation according to the invention are chosen from at least one of the following compounds: one or more sodium salts of $C_{10}$-$C_{16}$ carboxymethyl ether glycosides; a carboxymethyldodecyloxy sodium salt; a carboxymethyloctyloxy sodium salt and sodium lauryl sulfate (or sodium dodecyl sulfate—SDS).

In one particular embodiment, the biocidal formulation according to the invention contains nonionic and anionic surfactants, the carbon-based chain of which is between 6 and 20 carbon atoms. In one particular embodiment, this carbon-based chain is between 8 and 16 carbon atoms.

In one certain embodiment, the biocidal product according to the invention contains nonionic surfactants selected from alkyl polyethoxylates and/or alkyl polyglycosides and polyglycerol esters. Finally, in one preferred embodiment, the biocidal product according to the invention contains nonionic surfactants selected from alkyl polyethoxylates and/or polyglycosides and polyglycerol esters, the carbon-based chain of which comprises 6 to 20 carbon atoms. Examples of alkyl polyglycosides usable in the formulation according to the invention are D-glucopyranose alkyl $C_8$-$C_{10}$ alkyl glycosides and D-glucopyranose $C_{10}$-$C_{16}$ alkyl glycosides.

In another embodiment, the biocidal product according to the invention contains anionic surfactants selected from the acid salts of the type alkyl polyethoxylates/propoxylates and/or polyols of the polyglycoside and/or polyglycerol type. The number of hydrophilic units in order to have an advantageous HLB (hydrophilic-lipophilic balance) is between 1 and 10. In another preferred embodiment, the biocidal product according to the invention contains anionic scarf selected from alkyl carboxylates and alkyl sulfates, the carbon-based chain of which comprises 6 to 20 carbon atoms. Preferably, the polyglycosides used as nonionic surfactants in the concentrated biocidal formulation according to the invention are selected from $C_4$ to $C_{18}$ alkyl polyglycosides, and they are advantageously at least one of the compounds chosen from: a lauryl polyglycoside, such as lauryl glucoside (dodecyl glucoside, also known as n-dodecyl β-D-glucopyranoside); a myristyl polyglycoside, such as myristyl glucoside (tetradecyl β-D-glucopyranoside) and a caprylyl/capryl polyglycoside, such as octyl glucoside (n-octyl β-D-glucopyranoside).

The chelating agents which are part of the composition of the biocidal product according to the invention are conventional agents in the field of cleaning and disinfecting surfaces for domestic and professional use. They are selected from the chelating agents commonly used in biocidal products, such as citric acid derived from lemon juice or sorbic acid derived from sorb or oxalic acid derived from the roots or rhizomes of numerous plants (sorrel, beetroot, etc.), sequestering monomers or polymers such as chicory extracts. The olfactory properties of the biocidal products according to the invention are conferred by the presence of a natural fragrance derived from a renewable and biodegradable natural resource. These natural fragrances are essential oils, plant essences or plant extracts. Mention will in particular be made, by way of example, of mint A, mint N or eucalyptus G.

In one preferred embodiment, the concentrated biocidal formulation of plant origin contains:
between 0.01% and 20% of chelating agent;
between 0.03% and 25% of nonionic surfactants of alkyl polyglycoside, polyglycerol ester or sorbitan ester type;
between 0.03% and 25% of anionic surfactants of alkyl carboxylate type;
between 0.1% and 75% of lactic acid;
between 0.001% and 8% of natural fragrance;
and is completely biodegradable and completely derived from renewable agricultural plant resources. The biocidal activity of the lactic acid is then significantly increased by the presence of the surfactants and of the chelating agents.

In one preferred embodiment, the concentrated biocidal formulation of plant origin contains:
between 0.01% and 20% of chelating agent;
between 0.03% and 25% of nonionic surfactants of alkylpolyglycoside, polyglycerol ester or sorbitan ester type;
between 0.03% and 25% of anionic surfactants of alkyl carboxylate or alkyl sulfate type with or without propoxylated or ethoxylated residues;
between 0.1% and 75% of L-lactic acid;
between 0.001% and 8% of natural fragrance.

According to yet another embodiment, the concentrated biocidal formulation of plant origin contains:
0.4% of essential oils;
12% of nonionic surfactants of glycoside, polyglycerol ester or sorbitan ester type;
8% of anionic surfactants of the type such as salts of fatty acids with a chain containing between 12 and 18 carbon atoms;
20% to 40% of citric acid;
0% to 10% of lactic acid;
and it is completely biodegradable and completely derived from renewable agricultural plant resources.

A formulation containing the biocidal product according to the invention can be diluted from 1 to 500-fold in water depending on the use envisioned.

The formulations according to the invention conform to the European regulations in terms of effectiveness. They meet standards EN1040, EN1276, EN1650 and EN14476+A1 in dirty or clean conditions. These formulations pose no specific danger to humans and are not detrimental to the environment.

The biocidal formulations according to the invention are capable of being used at dilution levels and for action times which are comparable to those required by the professional market, are in accordance with the requisite biocidal effectiveness requirements, pose no specific danger on application, are biodegradable and are not ecotoxic after elimination.

The applications envisioned for the biocidal formulations according to the invention are based on a disinfectant action, but also a detergent, degreasing, emollient, olfactory, etc., action. Mention will be made, by way of examples, but without this list being exhaustive, of application of the formulations according to the invention to antifoam products for cleaning stonework structures, products for cleaning from pontoons and boat hulls the foams and algae which colonize them; disinfectant detergent solutions for all types of surface; solutions for hand hygiene by washing or by friction; solutions for disinfecting foodstuffs; solutions for disinfecting transport and farming premises, buildings and materials (products of animal origin, products of vegetable origin); solutions for disinfecting surfaces for the food-processing, cosmetics or pharmaceutical industry; disinfecting solutions for household waste premises and/or transport.

In one particular embodiment, the biocidal formulations according to the invention are used for hand hygiene, by washing or by friction, in liquid or semi-liquid form.

In one preferred embodiment, the biocidal formulations according to the invention are provided in concentrated liquid form. They can be highly diluted in water (for example 100-fold) without any other addition and with their activities being just as well preserved, depending on the application envisioned.

The present invention also relates to a substrate combined with a biocidal formulation according to the invention, allowing the application of said formulation on a surface to be cleaned and to be disinfected. This substrate can consist of a cloth, a wipe or a towel. On its substrate, the formulation according to the invention may be pure and be activated only once in the presence of water, or else be already diluted and ready to use.

According to another aspect, the present invention relates to a ready-to-use biocidal formulation obtained, by dilution with water, from the biocidal formulation previously presented in the context of the present invention and notable in that it contains:
    between 0.01% and 0.2% of chelating agent;
    between 0.03% and 0.1% of nonionic surfactants of glycoside, poly glycerol ester or sorbitan ester type;
    between 0.03% and 0.1% of anionic surfactants;
    between 0.1% and 0.5% of at least one organic acid;
and that it is completely biodegradable and completely derived from natural renewable agricultural resources.

Such a ready-to-use formulation demonstrates the effectiveness of the synergy of action of the ingredients of the mixture at very low concentrations. It is particularly advantageous to obtain the desired biocidal effect from such a highly diluted formulation, thereby making it possible to improve the selectivity by specifically eradicating the unwanted species.

Example

A concentrated formulation with biocidal activity according to the invention containing:
    0.4% of essential oils (mint N, eucalyptus G and/or mint A);
    12% of nonionic surfactants of glycoside type (D-glucopyranose $C_8$-$C_{10}$ alkyl glycosides and/or D-glucopyranose $C_{10}$-$C_{16}$ alkyl glycosides);
    8% of anionic surfactants of the type such as salts of fatty acids with a chain containing 12 to 18 carbon atoms (sodium salt(s) of $C_{10}$-$C_{16}$ carboxymethyl ether glycosides, carboxymethyldodecyloxy sodium salt, a carboxymethyloctyloxy sodium salt and/or sodium lauryl sulfate);
    20% of citric acid at 50%;
    10% of (L+) lactic acid.

The most severe classification for this concentrated biocidal substance is XiR38/41 according to the regulations in force for biocides. This biocide poses no significant danger to humans or to the environment compared with the biocidal substances on the market.

This formulation is to be diluted according to the surfaces to be cleaned, to be purified and to be disinfected. The active dilute form for the disinfecting function poses no known and/or regulated danger.

Biocidal Formulation Effectiveness Tests

1. Yeasts

This quantitative suspension test for evaluating the basic yeasticidal activity of the formulation according to the invention is carried out by a microbiology laboratory. This test is carried out in dirty conditions and in additional conditions.

Method: A dilution/neutralization method is applied to a formulation according to the invention. The neutralizing agent consists of sodium chloride (0.85% W/V) and $Na_2CO_3$ (0.1%), the volume being made up of distilled water.

The formulation according to the invention is diluted in physiological saline to the following concentrations: 0.25%, 0.5% and 1%.

The tests are carried out on a strain of *Candida albicans* (ATCC 90028) at a temperature of 20° C. (±1° C.). The contact time is limited to 5 minutes 10 seconds).

The interfering substance is bovine albumin (fraction V) in a proportion of 3.00 g/l. This constitutes the dirty condition.

Incubation at a Temperature of 25.0° C. (±0.2° C.)

Results: In accordance with the provisions of standard NF EN 1275 (April 2006), the concentrated formula according to the invention exhibits a yeasticidal activity in dirty conditions (3.00 g/l of bovine albumin) after 5 minutes of contact at 20° C. with respect to a reference *Candida albicans* strain for the concentration of 1%.

2. Viruses

This virucidal effectiveness test is carried out according to the methodology of standard NF EN 14476+A1 (January 2007) on an influenza H3N2 virus on 3 samples of ready-to-use disinfectant product, according to the formulation of the present invention.

The H3N2 strains and the H1N1 strains belong to the family of type A influenza viruses and exhibit great structural homology. Consequently, the results obtained on the H3N2 viruses can be extended to the H1N1 viruses.

Method: The test is carried out at 20° C. (±1° C.). The virus is titered in PFU/ml, i.e. in number of infectious viral particles per ml, and more commonly in logarithm of the viral titer. The contact time is 30 seconds. The samples are diluted in sterile distilled water.

The viral influenza strain is H3N2 A/Brisbane/10/2007 (Pasteur Institute) grown on MDCK cells at 36.5° C. under 5% CO2.

The interfering substance is bovine albumin (BSA 3.00 g/l).

The technique for stopping virucidal action is the addition of a solution containing $NaCO_3$, in a proportion of 70 g/l, pH 10.85 and 10 ml of stop solution for 10 ml of test solution.

Results: The 3 samples have a virucidal activity on the H3N1 strain and by extension on a strain of H1N1 type.

More particularly:
    sample 1 has a virucidal activity on the H1N1 influenza virus (model H3N2) at the concentration of 40% for 30 seconds of contact;
    sample 2 has a virucidal activity on the H1N1 influenza virus (model H3N2) at the concentration of 10% for 1 minute of contact;
    sample 3 has a virucidal activity on the H1N1 influenza virus (model H3N2) at the concentrations of 1% and 2% for 5 minutes of contact.

Moreover, given the experimental results obtained on the influenza A/H3N2 virus and a similarity in structure and in sensitivity to chemicals of negative RNA genome enveloped viruses, the products exhibiting virucidal activity demonstrated in this study on the influenza A/H3N2 virus can potentially inactivate the following enveloped viruses:
    the family orthomyxoviridae: influenza virus A, B and C
    the family paramyxoviridae: parainfluenza virus (1-4), respiratory syncytial virus (RSV).

Moreover, the products tested in this study could prove to be effective on other DNA genome enveloped viruses, such as the family Herpesviridae which comprises:

HHV 1 or HSV 1 (Herpes Simplex virus-1) responsible for orolabial herpes, HHV 2 or HSV 2 (Herpes Simplex virus-2) responsible for genital herpes, HHV 3 or VZV (Varicella Zoster virus) responsible for chickenpox (primary infection) and/or for shingles (re-infection), HHV 4 or EBV (Epstein-Barr virus) responsible for infectious mononucleosis, Burkitt's lymphoma or nasopharyngeal carcinoma, HHV 5 or CMV (cytomegalovirus) for mononucleosis syndrome, retinitis, serious infections in individuals who are immunodepressed or have undergone transplants, etc., HHV 6, responsible for roseola infantum, slapped cheek syndrome in children, HHV 7, very close to HHV 6 and which causes the same symptoms, HHV 8 or KSHV (Kaposi's sarcoma-associated herpesvirus), herpes virus associated with Kaposi's sarcoma observed in particular in individuals who are HIV seropositive.

3. Bacteria

This quantitative suspension test for evaluating the bactericidal activity of the formulations according to the present invention is carried out by a microbiology laboratory.

Method: A dilution/neutralization method is applied to a formulation according to the invention. The neutralizing agent consists of sodium chloride (0.85% W/V) and $Na_2CO_3$ (0.1%), the volume being made up with distilled water.

The formulation according to the invention is diluted in physiological saline to the following concentrations: 0.25%, 0.5%, 0.75% and 1%.

The tests are carried out on strains of *Staphylococcus aureus* (ATTC 6538) *Escherichia coli* (ATCC 10536), *Enterococcus hirae* (ATCC 10541) and *Pseudomonas aeruginosa* (ATCC 15442) at a temperature of 20° C. (±1° C.). The contact time is limited to 5 minutes (±10 seconds).

The interfering substance is bovine albumin (fraction V) in a proportion of 3.00 g/l. This constitutes the dirty condition.

Incubation at a Temperature of 37.0° C.

Results: According to the indications of standard NF EN 1276 (October 1997), a concentrated disinfecting formula according to the formulation of the present invention has a bactericidal activity in dirty conditions (3.00 g/l of bovine albumin) after 5 minutes of contact at 20° C. with respect to the 4 reference strains tested for the test concentration of 1%. The limiting microorganism is *Staphylococcus aureus* (ATCC 6538).

2. Biodegradability

This test is an evaluation, in aqueous medium, of the ultimate aerobic biodegradability of a sample of the concentrated formulation according to the invention. This test is carried out according to the provisions of OECD method 301 B at the concentration of 100.0 g/l corresponding to an organic carbon content of 10 mg/l. The theoretical amount of carbon dioxide formed ($CO_2Th$) in the "concentrated disinfectant detergent for floors, surfaces and materials at 10 mg/l of DOC" test is equal to 33.0 mg/l.

The physicochemical analysis is carried out according to standard ASTM D5291.

FIG. 1 represents the curves of results of degradation with respect to $CO_2Th$.

Results: the test is considered to be valid because

The percentage degradation of the reference substance (sodium acetate) is greater than 60% (81%) on the fourteenth day.

The amount of $CO_2$ given off by the blank control is acceptable: about 34 mg/l after 28 days (value not to exceed: 40 mg/l).

The sample of the formulation according to the invention, at 10 mg/l of DOC, is not an inhibitor of the sodium acetate degradation, since the "concentrated disinfectant detergent for floors, surfaces and materials at 10 mg/l of DOC 4+sodium acetate 100 mg/l" mixture is 72% degraded after 14 days (condition for validity of the standard: degradation greater than 35% after 14 days).

CONCLUSION

The evaluation, in aqueous medium, of the "ultimate" biodegradability of the sample tested according to OECD guideline 301 B gives the following results:

the maximum degree of biodegradation of the sample at 10 mg/l of DOC is equal to 100% after 36 days of incubation;

the biodegradation time (corresponding to 90% of the maximum degree of biodegradation) is approximately 25 days;

according to OECD guideline 301 B, the sample tested is considered to be readily biodegradable (threshold of 60% of theoretical $CO_2$ release exceeded after 7 days of incubation).

The degree of biodegradability measured takes into account the entire formulation: in fact, there is no degradation by-product since the formulation is exclusively composed of carbon, oxygen and hydrogen atoms originating from plant extracts. This is a true measure of ultimate biodegradability.

The invention claimed is:

1. A biocidal composition comprising:
   a chelating agent, in an amount of 0.05-0.2 wt % of said composition, wherein said chelating agent is selected from the group consisting of succinic acid and sorbic acid;
   a nonionic surfactant, in an amount of 0.03-0.12 wt % of said composition, wherein said nonionic surfactant contains a carbon-based chain of between 6 and 20 carbon atoms and is selected from the group consisting of alkyl polyglycoside, polyglycerol ester and sorbitan ester;
   an anionic surfactant, in an amount of 0.02-0.08 wt % of said composition, wherein said anionic surfactant contains a carbon-based chain of between 6 and 20 carbon atoms and is an alkali or alkaline earth-metal carboxylic salt selected from a group consisting of alkyl polyethoxylates, propoxylates, polyols of polyglycoside, polyols of polyglycerol combined with a chemical so as to form alkyl carboxylate surfactants or alkyl sulfate surfactants;
   lactic acid, in an amount of 0.025-0.1 wt % of said composition;
   citric acid, in an amount of 0.025-0.1 wt % of said composition;
   a natural fragrance, in an amount of 0.001-0.004 wt % of said composition, wherein the natural fragrance is selected from the group consisting of essential oils, plant essences and plant extracts; and
   water, in an amount of 99.00 to 99.75 wt % of said composition;

wherein said composition has bactericidal activity after at least five minutes of contact at 20 degrees Celsius on a surface to which said composition is applied.

2. The biocidal composition of claim 1, wherein said natural fragrance is an essential oil.

3. The biocidal composition of claim 1, wherein the composition has a biodegradation time of approximately 25 days for 90% of a maximum degree of biodegradation.

4. A biocidal composition comprising:
- a chelating agent, in an amount of 0.05-0.2 wt % of said composition, wherein said chelating agent is selected from the group consisting of succinic acid and sorbic acid;
- a nonionic surfactant, in an amount of 0.03-0.12 wt % of said composition, wherein said nonionic surfactant contains a carbon-based chain of between 6 and 20 carbon atoms and is selected from the group consisting of alkyl polyglycoside, polyglycerol ester and sorbitan ester;
- an anionic surfactant, in an amount of 0.02-0.08 wt % of said composition, wherein said anionic surfactant contains a carbon-based chain of between 6 and 20 carbon atoms and is an alkali or alkaline earth-metal carboxylic salt selected from a group consisting of alkyl polyethoxylates, propoxylates, polyols of polyglycoside, polyols of polyglycerol combined with a chemical so as to form alkyl carboxylate surfactants or alkyl sulfate surfactants;
- lactic acid, in an amount of 0.025-0.1 wt % of said composition;
- citric acid, in an amount of 0.025-0.1 wt % of said composition;
- a natural fragrance, in an amount of 0.001-0.004 wt % of said composition, wherein the natural fragrance is selected from the group consisting of essential oils, plant essences and plant extracts; and
- water, in an amount of 99.00 to 99.75 wt % of said composition;
  - wherein said composition has yeasticidal activity after at least five minutes of contact at 20 degrees Celsius on a surface to which said composition is applied.

5. The biocidal composition of claim 4, wherein the composition has a biodegradation time of approximately 25 days for 90% of a maximum degree of biodegradation.

6. A biocidal composition comprising:
- a chelating agent, in an amount of 0.05-0.2 wt % of said composition, wherein said chelating agent is selected from the group consisting of succinic acid and sorbic acid;
- a nonionic surfactant, in an amount of 0.03-0.12 wt % of said composition, wherein said nonionic surfactant contains a carbon-based chain of between 6 and 20 carbon atoms and is selected from the group consisting of alkyl polyglycoside, polyglycerol ester and sorbitan ester;
- an anionic surfactant, in an amount of 0.02-0.08 wt % of said composition, wherein said anionic surfactant contains a carbon-based chain of between 6 and 20 carbon atoms and is an alkali or alkaline earth-metal carboxylic salt selected from a group consisting of alkyl polyethoxylates, propoxylates, polyols of polyglycoside, polyols of polyglycerol combined with a chemical so as to form alkyl carboxylate surfactants or alkyl sulfate surfactants;
- lactic acid, in an amount of 0.025-0.1 wt % of said composition;
- citric acid, in an amount of 0.025-0.1 wt % of said composition;
- a natural fragrance, in an amount of 0.001-0.004 wt % of said composition, wherein the natural fragrance is selected from the group consisting of essential oils, plant essences and plant extracts; and
- water, in an amount of 99.00 to 99.75 wt % of said composition;
  - wherein said composition has virucidal activity against an H3N2 influenza strain after at least five minutes of contact at 20 degrees Celsius on a surface to which said composition is applied.

7. The biocidal composition of claim 6, wherein the composition has a biodegradation time of approximately 25 days for 90% of a maximum degree of biodegradation.

* * * * *